US005837520A

United States Patent [19]
Shabram et al.

[11] Patent Number: 5,837,520
[45] Date of Patent: Nov. 17, 1998

[54] METHOD OF PURIFICATION OF VIRAL VECTORS

[75] Inventors: Paul W. Shabram, Olivenhain; Bernard G. Huyghe, San Diego, both of Calif.; Xiaodong Liu, New York, N.Y.; H. Michael Shepard, Rancho Santa Fe, Calif.

[73] Assignee: Canji, Inc., San Diego, Calif.

[21] Appl. No.: 400,793

[22] Filed: Mar. 7, 1995

[51] Int. Cl.$^6$ .............................. C12N 7/02; C12N 7/00; C12N 15/00

[52] U.S. Cl. .................... 435/239; 435/235.1; 435/69.1; 435/320.1; 435/803

[58] Field of Search ............................... 435/235.1, 239, 435/320.1, 803, 69.1; 424/93.2; 530/412

[56] References Cited

U.S. PATENT DOCUMENTS 4,569,794   2/1986   Smith et al. ........................... 260/113

OTHER PUBLICATIONS

Albrechten et al., *J Virological Methods*, "Purification of plant virus coat proteins by high performance liquid chromatography", 28:245–256 (1990).
Hewish et al., *J. Virological Methods*, "Purification of Barley Yellow Dwarf virus by gel filtration on Shephracryl$^R$ S–1000 superfine" 7:223–228 (1983).
Hjorth and Moreno–Lopez, *J. Virological Methods*, "Purification of bovine papilloma virus by gel filtration on Sephacryl$^R$ S–1000 Superfine" 5:151–158 (1982).
Najayou et al., *J. Virological Methods*, "Purification of measles virus by affinity chromatography and by ultracentrifugation: a comparative study" 32:67–77 (1991).
Diaco et al., *J. Gen. Virol.*, "Purification of soybean mosaic virus by affinity chromatography using monoclonal antibodies" 67:345–351 (1986).
Fowler, *J. Virological Methods*, "Purification of biologically active Epstein–Barr virus by affinity chromatography and non–ionic Density gradient centrifugation" 11:59–74 (1985).
Philipson, *Virology*, "Adenovirus assay by the fluorescent cell–counting procedure" 15:263–268 (1961).
Haruna et al., *Virology*, "Separation of a adenovirus by chromatography on DEAE–cellulose" 13:264–267 (1961).
Klemperer and Pereir, *Virology*, "Study of Adenovirus antigen fractionation by chromatography on DEAE cellulose" 9:536–545 (1959).
Philipson, *Virology*, "Separation on DEAE cellulose of components associated with adenovirus reproduction", 10:459–465 (1960).
Wills et al., *Human Gene Therapy*, "Development and characterization of recombinant adenoviruses encoding human p53 for gene therapy of cancer" 5:1079–1088 (1994).
Laver et al., *Virology*, "Purification and properties of chick embryo lethal orphan virus (an avian adenovirus)" 45:598–614 (1971).
Maizel et al., *Virology*, "The polypeptides of Adenovirus 1: Evidence for multiple protein components in the virion and a comparison of types 2, 7A and 12" 36:115–125 (1968).
Belew et al., *Anal. Biochem.*, High performance analytical applications of immobilized metal ion affinity chromatography 164:457–465 (1987).
Kato et al., *J. Chrom.*, "High–performance metal chelate affinity chromatography of proteins" 354:511–517 (1986).
Seth, *Journal of Virology*, "Adenovirus–dependent release of choline from plasma membrane vesicles at an acidic pH is mediated by the penton base protein" 68:1204–1206 (1994).
Lynn, *BioTechniques*, "A BASIC computer program for analyzing endpoint assays" 12:880–881 (1994).
Orkin et. al. Report and Recommendations of the Panel to . . . Genetherapy. NIH Dec. 7, 1995.
Marshall. Science vol. 269. 25 Aug. 1995.
Huyghe et al. Human Gene Therapy. 6 (1403–1416) Nov. 1995.
Alberts et al. Molecular Biology of the Cell. 3$^{rd}$ Ed. Garland Publishing. New York. 1994.
Maramarosch et al. Methods in Virology vol. II. Academic Press. New York 1967.

*Primary Examiner*—Jasemine C. Chambers
*Assistant Examiner*—Karen M. Hauda
*Attorney, Agent, or Firm*—Townsend and Townsend and Crew LLP

[57] ABSTRACT

The invention provides a method for purifying viral vectors containing therapeutic genes for use in gene therapy. The invention comprises a method of purification from a cell lysate of a recombinant viral vector containing a therapeutic gene, which comprises: a) treating said lysate with an enzymatic agent that selectively degrades both unencapsulated DNA and RNA; b) chromatographing the treated lysate from step a) on a first resin; and c) chromatographing the eluant from step b) on a second resin; wherein one resin is an anion exchange resin and the other is an immobilized metal ion chromatography (IMAC) resin.

27 Claims, 6 Drawing Sheets

METHOD OF PURIFICATION OF VIRAL VECTORS

BACKGROUND OF THE INVENTION

The treatment of disease by gene therapy has moved from the theoretical to the practical realm. The first human gene therapy trial was begun in September 1990 and involved transfer of adenosine deaminase (ADA) gene into lymphocytes of patients with defects of this enzyme. Lack of ADA activity results in immune deficiency. Of several methods for delivering therapeutic genes to diseased cells, viral vectors hold out particular promise. Tumor suppressor genes are being investigated for treating cancerous cells. Viral vectors containing such tumor suppressor genes are being evaluated as potential therapeutics in the field of cancer therapy. Recently, adenovirus vectors have received particular attention as an advantageous vector for the delivery of such tumor suppressor genes and other biological response modifiers. As studies of cancer gene therapy progress to clinical trials, larger and larger quantities of purified viral vectors are needed. One problem in producing suitable quantities of vectors for such trials is the purification of the particles from the cell lysates in which the viral particles are produced.

Specifically, purification of these vectors has historically been performed by using density-based ultracentrifugation methods. While this method has proven effective for use as a research tool, it is not feasible as a method for industrial scale production. Meeting the demands for material in the future would lead to prohibitive costs unless a new purification scheme could be developed. One alternative to ultracentrifugation is chromatographic techniques for purification of infectious viral particles.

The use of size exclusion chromatography for purification of various plant viruses has been demonstrated either as a stand alone technique or to augment density gradient centrifugation (Albrechtsen et al., *J. Virological Methods* 28:245–256 (1990); and Hewish et al., *J. Virological Methods* 7:223–228 (1983)). Size exclusion appears promising for bovine papilloma virus (Hjorth and Mereno-Lopez, *J. Virological Methods* 5:151–158 (1982)); and has been shown to be a superior method for the purification of tick-borne encephalitis virus (Crooks et al., *J. Chrom.* 502:59–68 (1990)). The use of size exclusion chromatography has not yet become widespread, but is currently being employed for large scale production of recombinant retroviruses (Mento, S. J., Viagene, Inc. as reported at the 1994 Williamsburg Bioprocessing Conference). Affinity chromatography, mostly using monoclonal antibodies (Mab), has been reported to be an effective method for the purification of antigens of viral origin (Najayou et al., *J. Virological Methods*, 32:67–77. 1991). Soybean mosaic virus (a virus which can survive pH 3) can be recovered using Mab affinity chromatography (Diaco et al., *J. Gen. Virol.* 67:345–351. 1986). Fowler (*J. Virological Methods.* 11:59–74. (1985)) used affinity chromatography and density gradient centrifugation to purify Epstein Barr virus.

Adenoviruses are large (diameter of approximately 80 nm) and somewhat fragile. A large literature base dealing with the relationship of structure to function has accumulated (for reviews see Philipson, *Virology* 15:263–268 (1961) and Horwitz, *Virology* (Second Edition) Raven Press Ltd, New York (1990)). Little has been reported in the literature about chromatographic purification of live adenoviruses. Haruna et al. (*Virology* 13:264–267 (1961)) reported using DEAE ion exchange chromatography for purification of types 1, 3 and 8 adenoviruses while Klemperer and Pereir (*Virology* 9:536–545 1959)) and Philipson (*Virology* 10:459–465 (1960)) reported difficulties using the same method with other types of adenoviruses. Poor resolution and poor yield are important problems with this methodology that has prevented its use in large-scale production.

Thus, a need exists for a chromatographic method for purifying viral vectors such as adenovirus vectors.

SUMMARY OF THE INVENTION

One obstacle to the successful practice of gene therapy is the availability of purified viral vectors to deliver therapeutic genes. The present invention solves that problem by the unexpected and surprising discovery that viral vectors containing therapeutic genes can be purified sufficiently for therapeutic and/or prophylactic use using a three step process comprising: enzymatically treating the cell lysate comprising the viral vector containing the therapeutic gene; chromatographing the enzymatically treated cell lysate on a first resin; and chromatographing the eluate from the first column on a second resin. The resulting purified viral vectors having the therapeutic gene retained their infectivity during and after chromatographic treatment and are able to effect gene transfer. For the first time it was found using the purification method of this invention that the chromatographically purified viral vector containing the therapeutic gene is as pure and active as a viral vector is purified using a three day ultracentrifugation. The purification method of this invention provides several advantages over existing methods including quality of purified viral vector, consistency, decreased process time and the ability to process large amounts of sample. Furthermore, because this novel purification scheme is based on the surface characteristics of the virion it is broadly applicable to other virions using the teaching of this invention as well as to virions containing different internal DNA constructs with different therapeutic genes. This breakthrough purification method is an important aspect in bulk commercialization of gene therapy.

Therefore, the invention provides a method of purifying viral vectors containing therapeutic genes for use in gene therapy. In one embodiment, the invention comprises a method of purification from a cell lysate of a recombinant viral vector containing a therapeutic gene, which comprises: a) treating said lysate with an enzymatic agent that selectively degrades both unencapsulated DNA and RNA; b) chromatographing the treated lysate from step a) on a first resin; and c) chromatographing the eluant from step b) on a second resin; wherein one resin is an anion exchange resin and the other is an immobilized metal ion chromatography (IMAC) resin.

In an alternative embodiment a hydrophobic interaction chromatography resin may be substituted for the immobilized metal ion chromatography resin and/or a cation exchange resin may be substituted for the anion exchange resin.

In an alternative embodiment the enzymatically treated cell lysate undergoes a filtration step adding a fourth step to the three step method.

In a more preferred embodiment the viral vector being purified is an adenoviral vector containing a therapeutic gene. In a still more preferred embodiment the adenoviral vector is a recombinant type 5 adenovirus with an internal DNA construct including a tumor suppressor gene.

DETAILED DESCRIPTION OF THE INVENTION

Figure 1:
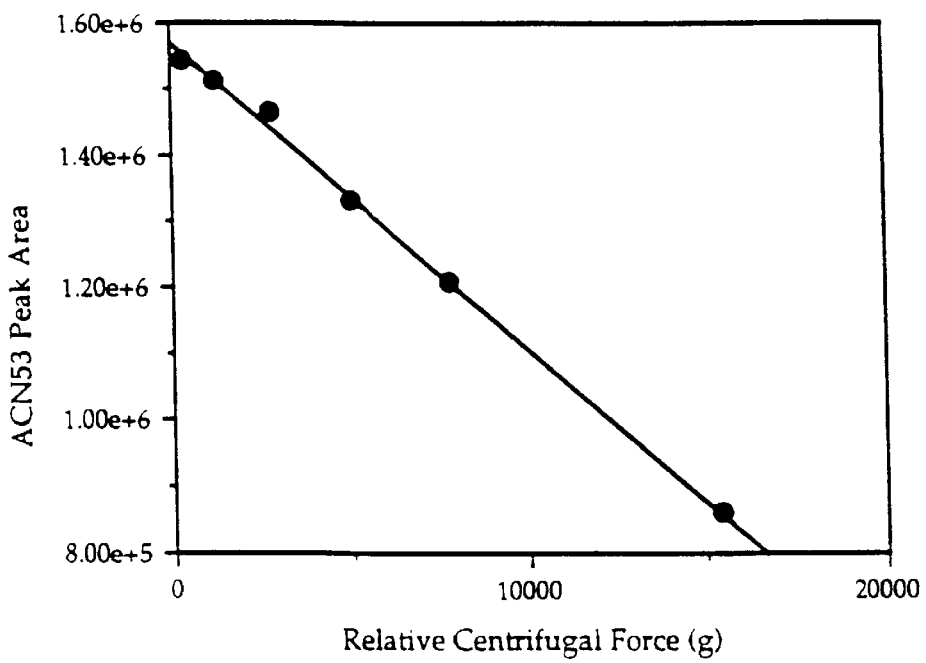
FIG. 1: Recovery of ACN53 from the supernatant of centrifuged crude infected cell lysate which was centrifuged for 5 minutes at different speeds in an Eppendorf centrifuge model 5415c at 40°. Analysis for ACN53 was by analytical anion exchange.

This invention is directed to a method for purification of a recombinant viral vector containing a therapeutic gene from a cell lysate, which comprises:

a) treating the cell lysate with an enzymatic agent that selectively degrades both unencapsulated DNA and RNA; b) chromatographing the treated lysate from step a) on a first resin; and c) chromatographing the eluant from step b) on a second resin; wherein one such resin is an anion exchange resin and the other is an immobilized metal ion affinity resin.

The term "viral vector" means a recombinant virus that has had some or all of the genes in the native genome removed such that the virus is replication-incompetent. Furthermore, the viral vector shall mean viruses wherein the recombinant viral genome contains a DNA encoding a therapeutic gene such that the viral vector is used to transfer the therapeutic gene to a desired human cell for gene therapy. Representative vectors include those that will infect mammalian, and especially human, cells, and are derived from viruses chosen from the group consisting of retroviruses, adenoviruses, herpes viruses and avipox viruses. Retroviral and adenoviral vectors are preferred. Adenoviral vectors, especially type 2 and type 5 adenoviral vectors, are especially preferred. The recombinant type 5 adenoviral vectors are the most preferred.

The term "therapeutic gene" means genes or functional fractions thereof encoding molecules which have a desired therapeutic effect. For example, a gene which either by its absence or mutation causes an increase in pathological cell growth or proliferation of cells. A therapeutic gene as used herein would replace such an absent or mutated gene. Therapeutic genes may give rise to their therapeutic effect either by remaining extrachromosomal such that the gene will be expressed by the cell from the extrachromosomal location or the gene may be incorporated into the genome of the cell such that it recombines with the endogenous gene. Such genes include tumor-suppressor genes, including those chosen from the group consisting of Rb, Rb mutants, p53, p53 mutants, DCC, NF-1, Wilm's tumor, NM 23, BRCA-1, BRCA-2, BRUSH-1, p56, H-NUC, thyroid hormone receptor gene, retenoic acid receptor gene, genes encoding p130, p107, and p85. Other gene replacement or supplementation strategies include adenosine deaminase (ADA), thymidine kinase (TK), genes encoding various cytokines such as γ-interferon, α-interferon, IL-2 and other hormones.

Therapeutic gene is also understood to include DNA encoding a ribozyme. Such DNA constructs encode an RNA enzyme which binds and destroys the RNA of selected positively-acting growth regulatory genes such as (1) oncogenes or proto-oncogenes selected from the group consisting of, but not limited to, the following: c-myc, c-fos, c-jun, c-myb, c-ras, Kc and JE; (2) growth factor receptor genes selected from the group consisting of, but not limited to, epidermal growth factor, platelet derived growth factor, transferrin and insulin.

Preferred therapeutic genes are the tumor suppressor genes, with most preferred tumor suppressor genes being Rb, Rb mutants, p53, p53 mutants, BRUSH-1, p56, BRCA-1, BRCA-2, p16 and p21.

The term "cell lysate" means a collection of cells, including host cells which contain a vector, preferably a viral vector, which cells have been removed from their growth environment and have had their cell membranes disrupted by physiological or chemical means.

The term "enzymatic agent" means a compound or mixture that selectively degrades unencapsulated DNA and RNA, while not disrupting the recombinant viral vectors to the extent they are not infectious and are unable deliver an intact copy of the therapeutic gene to the desired target cell. Such an enzymatic agent is generally a combination of one or more enzymes referred to as endonucleases or DNAses or RNAses. Benzonase™ (Nycomed Pharma A/S, Hvidovre, Denmark) is a preferred enzymatic reagent.

The term "anion exchange resin" shall mean a positively-charged organic moiety covalently cross-linked to an inert polymeric support. Representative organic moieties are drawn from primary, secondary, tertiary and quaternary amino groups; such as trimethylaminoethyl (TMAE), diethylaminoethyl (DEAE), dimethylaminoethyl (DMAE), and other groups such as the polyethyleneimine (PEI) that already have, or will have, a formal positive charge within the pH range of approximately 5 to approximately 9.

Similarly, representative negatively changed organic groups are chosen from the group consisting of carboxymethyl and sulfomethyl and other groups that have, or will have, a formal negative charge within the pH range of about 5 to about 9

The support material should be one that is easily derivatizable and possess good mechanical strength. The material can be a natural polymeric substance, a synthetic polymer or co-polymer, or a mixture of natural and synthetics polymers. The support can take the shape of porous or non-porous particles, beads, membranes, disks or sheets. Such supports include silica, hydrophilic polymer (MonoBeads®, Pharmacia, Piscataway, N.J.), cross-linked cellulose (e.g. Sephacel®), cross-linked dextran (e.g. Sephadex®) cross-linked agarose (e.g. Sepharose®), polystyrene, or a co-polymer such as polystyrene-divinylbenzene or one composed of oligoethyleneglycol, glycidylmethacrylate and pentaerythroldimethacrylate, to which are grafted polymerized chains of acrylamide derivatives (the latter co-polymer is known as a "tentacle" support).

The resins can be used in a traditional (gravity) column chromatography or high pressure liquid chromatography apparatus using radial or axial flow, fluidized bed columns, or in a slurry (batch) method. In the latter method, the resin is separated from the sample by decanting or centrifugation or filtration or a combination of methods. The viral vectors can be purified then eluted from these resins by an increasing salt gradient, preferably a gradient of sodium chloride.

Examples of suitable anion exchange resins include Fractogel® (E. Merck, Gibbstown, N.J.) resins derivatized with either DEAE or DMAE; Fractogel® EMD Tentacle resins derivatized with DEAE, DMAE, or TMAE; Toyopearl® (TasoHaas, Montgomeryville, Pa.) resins derivatized with DEAE or QAE; Acti-Disk® (Whatman, Clifton, N.J.) supports derivatized with Quat, DEAE or PEI; Sepharose® (Pharmacia, Piscataway, N.J.) resins derivatized with DEAE; Sephacel® (Pharmacia, Piscataway, N.J.) resins derivatized with DEAE; and Sephadex®) resins derivatized with DEAE and QAE. Preferred anion exchange resins are derivatized with the DEAE group, and further preferred columns are the Fractogel, Toyopearl and Streamline™ (Pharmacia, Piscataway, N.J.) DEAE resins.

Similarly, the term "cation exchange resin" means a negatively-charged organic moiety covalently cross-linked to an inert polymeric support.

Representative negatively-charged moieties include the carboxymethyl (CM) and the sulfomethyl (SP) groups. Other organic moieties that have, or will have, a formal negative charge in the ph range of about 5.0 to about 9.0 is also included within the definition. The above discussion for the support and the method of use for the anion exchange resin applies equally to the cation exchange resin. Examples of suitable commercially- available cation exchange resins include Sepharose, Sephacel and Sephadex covalently linked with either a CM or an SP group.

The term "Immobilized metal ion affinity chromatography" ("IMAC") resin refers to an inert natural or synthetic polymeric support covalently cross-linked with a metal chelating group. The metal chelating groups are those known in the art to bind to zinc, nickel, copper, cobalt, calcium or magnesium ions in the formal (+2) oxidation state. Such groups include the iminodiacetic (IDA) group, the tris(carboxymethyl)ethylenediamine (TED) group, the N-(hydroxyethyl) ethylenediaminetriacetic group, and derivatives such as the N-(methyl), and the N-(hydroxymethyl) IDA groups. These groups can be cross-linked to the natural or synthetic polymeric support by standard aliphatic ether linkages and reagents, such as bisoxirane, epichlorhydrin, and 1,4-bis-(2,3-epoxypropoxy) butane. For the method of the invention, the chelating groups can be bound to any of the above-listed metals, with zinc the preferred metal. The description of the chemical composition, physical form and uses of the polymeric supports described above for the term "anion exchange resin" applies to the IMAC resin as well. Cross-linked agarose and the "tentacle" supports are preferred. The viral vectors can be eluted from the IMAC column by adding increasing concentrations of competing chelating agents such as imidazole, histamine, glycine, or ammonium chloride, or, alternatively the pH of the eluant can be raised or lowered, as long as the extremes of the range of the ph gradient used remain from about 5 to about 9. Examples of commercially-available products that can be used in the instant method include the Acti-Disk IDA cartridge (Whatman), Fractogel AF chelate, and Toyopearl AF chelate IMAC resins.

Furthermore, the preferred conditions for the immobilized metal affinity ion resin for the purification of the viral vectors such as type 5-adenovirus derived vector on DEAE had the resin charged with a divalent metal cation chosen from the group consisting of cobalt, nickel, copper, zinc, calcium and magnesium and further wherein the resin is an IDA or TED cross-linked agarose resin, especially an IDA agarose resin that is charged with zinc ion.

A hydrophobic interaction chromatography ("HIC") can be substituted for the IMAC resin in the instant method. Such a resin has lower alkyl or aryl groups covalently bound through a non-polar group, such as an aliphatic ether, to an inert polymeric support. Lower alkyl groups such as methyl, propyl, n-butyl, neo-pentyl, and octyl and the phenyl group are examples of the interactive group on the instant resin. Butyl is the preferred interactive group. The chemical composition, physical form and method of use for the supports described In the definition of the term "anion-exchange resin" above also apply to the HIC resins. Cross-linked agarose, hydroxylated polyether, hydrophilic media and silica are the preferred supports with cross-linked agarose the most preferred. The viral vectors can be purified then eluted from the HIC resin by a decreasing salt gradient, with ammonium sulfate the preferred salt. Examples of commercially available HIC columns useful for the current invention include the cross-linked agarose columns such as Phenyl-, Butyl and Octyl Sepharose, and Toyopearl (Phenyl, Propyl, and Butyl) and Fractogel (Propyl or Phenyl).

As mentioned above, in the instant invention the IMAC or HIC resin can be used before or after the anion exchange resin. If used before, the salt concentration of the eluant from the HIC or IMAC resin should diluted to about 450 millimolar or less in order to prevent premature stripping of viral particles from the exchange resin.

The term "buffer" or "buffered solution" refers to a mixture of acid and base which when present in a solution reduces or modulates changes in pH that would otherwise occur in the solution when acid or based is added. In one embodiment, the cell lysate is maintained in a buffered solution. Suitable buffers are those that can maintain the pH of the resultant solution between about 5.0 and about 9. 0. Such buffers are commercially available and include phosphate, MES, HEPES, MOPS, Borate, TRIS, BES, ADA, ACES, PIPES, MOPSO, BIS-TRIS PROPANE, BES, TES, DIPSO, TAPSO, TRIZMA, HEPPSO, POPSO, TEA, EPPS, TRICINE, GLYCYLGLYCINE, BICINE, TAPS, and the like. Preferred buffers include the phosphate, MES, HEPES, MOPS, borate, and TRIS, with HEPES being the most preferred.

The use of chromatography for the purification of viral vectors, such as an adenoviral vector referred to as Type 5, for use in gene therapy has been shown to be an effective alternative to cesium chloride density gradient ultracentrifugations. There are several advantages related to this methodology, including quality, consistency, decreased process time, system automation, and the ability to process large amounts of crude lysate. The purification scheme described in this invention selects for product based on the surface characteristics of the virion. These characteristics do not change with different internal DNA constructs, e.g. having different therapeutic genes in the construct, therefore leading to similar chromatographic behaviors. In other words, the chromatography is unaffected by the nature of the therapeutic gene inserted inside the vector.

The anion exchange resins immobilized metal ion affinity chromatography resins cation exchange resins and hydrophobic interaction chromatography resins are cleaned using methods known to the ordinarily skilled artisan. By way of example, DEAE is treated first with NaOH then HCI and finally with NaCI. The IZAC is first treated with EDTA then NAOH, HCL, NaCI flushing with $H_2O$ in between each step. The columns are equilibrated in appropriate buffers using appropriate binding conditions. Columns are loaded with sample in a buffer such that the product will bind to the resin by controlling pH and salt concentration for DEAE and by controlling pH, salt concentration and divalent metal ion concentration for the immobilized metal ion affinity column. The columns are washed to remove contaminants and may be reused.

Other embodiments of the instant invention include the additional step of filtering the cell lysate after it is treated with the enzymatic agent. In an alternative embodiment the cell lysate is buffered before treatment with Benzonase at a pH between about 5.0 and about 9.0 before applying it to the first resin. These embodiments are preferred for purifying a recombinant viral vector derived from either a retrovirus or a adenovirus, and especially so when the vector is derived from an adenonvirus, and such a vector contains a tumor suppressor gene.

Further embodiments for purifying an adenoviral-derived vector containing a tumor suppressor gene are those when the treated, buffered cell lysate is first chromatographed over an anion exchange resin followed by chromatography over a immobilized metal affinity resin. These conditions are preferred especially when the recombinant viral vector is derived from either a type 2 or type 5 adenovirus, and especially a type 5 adenovirus.

The enzymatic agent used to treat the cell lysate is one or more enzymes, especially those chosen from the group consisting of RNAse and DNAse or a mixture of endonucleases as would be known to the ordinarily skilled artisan. The preferred enzymatic agent for use in this embodiment is Benzonase™, a recombinant non-specific nuclease which cleaves both RNA and DNA.

Finally, an especially preferred method of the one described in the preceding paragraphs is where the type 5 adenoviral-derived recombinant viral vector has a genome containing the wild-type p53 gene.

EXPERIMENTAL SECTION

Procedure 1

Preparation of ACN53 Standard Material (CsCI-ACN53)

Standard recombinant Adenovirus Type 5 designated ACN53 is a vector derived from a Type 5 Adenovirus which has the F1 coding sequence with a 1.4-kb full length p53 cDNA driven by the human cytomegalovirus promoter (Wills et al., *Human Gene Therapy* 5:1079–1088 (1994)). Virus was prepared by a 3-step centrifugation procedure as described (Laver et al., *Virology* 45:598–614 (1971)) with the following modifications. Infected cells were lysed by 3 cycles of freeze-thaw and centrifuged at 15,000 rpm for 10 min, 4° C. in a Sorvall RC-5B centrifuge. The pellet was discarded, and the supernatant was treated with Benzonase™ (American International Chemical, Natick, Mass.) at 133 U/mL for 30 min at room temperature. The treated material was then layered onto a 1.25 gm/mL and 1.40 gm/mL CsCI discontinuous step gradient in 10 mM Tris pH 8.1 and centrifuged at 30,000 rpm for 75 min, 10° C. in a Sorvall TST 41-14 rotor. The virus band from each tube was collected, pooled, mixed with 1.35 gm/mL CsCI (in 10 mM Tris pH 8.1) and centrifuged overnight at 45,000 rpm in a Beckman VTi 50 rotor at 10° C. The virus band from each tube was collected and recentrifuged at 45,000 rpm as before for an additional 4 hrs. The final virus pool from this step was dialyzed extensively against phosphate buffered saline (PBS) supplemented with 2% sucrose and 2 mM $MgCl_2$ at a temperature of 4° C. The purified virus was used to infect human embryonic kidney 293 cells (available from American Type Culture Collection), as described below in Procedure 2.

Procedure 2

Production of Infected ATCC 293 Cells, Harvest and Lysis

ATCC 293 (ATCC CRL 1573) cells were grown in a Cell Factory™ (Nunc, Ruskilde, Denmark) in a $CO_2$ incubator in 1.5L of medium consisting of DME high glucose medium containing 10% Hyclone bovine serum defined supplemented, 2 mM glutamine (Irvine Scientific, Santa Ana, Calif.), 1 mM sodium pyruvate (Irvine Scientific). No antibiotics were added to the medium.

Two to two and a half days after seeding the Cell Factory™, when cell monolayers reached about 50–60% confluency, the cells were infected with a multiplicity of infection (MOI) of 5 to 10 infectious units per cell in 500 mL of fresh medium. The virus was added to the medium, mixed thoroughly, and introduced to the cells in the unit.

When cell monolayers from Preparation 1 showed signs of detachment is from the surface of the Cell Factory™ (usually at 3 to 4 days post-infection), the cells were harvested by gentle tapping and were centrifuged in a Beckman TJ-6 at 1500 rpm for 5 min. They were washed once with serum free media, pelleted again, and resuspended in 25 mL of 50 mM Tris buffer pH 8.0/150 mM NaCI, 2 mM $MgCl_2$, 2% sucrose for use in the preparation of ultracentrifuge-derived standard virus. Samples destined for use in the procedures of Examples 1 through 3 were resuspended in 25 mL of 50 mM HEPES buffer pH 7.5/150 mM NaCI, 2 mM $MgCl_2$, 2% sucrose. The cells were lysed at this point by 3 cycles of freeze-thaw. Following the third cycle, cellular debris was removed by centrifugation in a Beckman TJ-6 at 1500 rpm for 5 min. at a temperature of 4° C.

Procedure 3

Western Blot Analysis of Samples Containing Recombinant Adenovirus Particles An SDS-PAGE gel was run as described in Example 3, Procedure F with approximately the same loading as that of a silver stained gel. The bands were then transferred to a PVDF membrane pre-wetted in 100% methanol and equilibrated in Tris-buffered saline (TBS). The gel was also equilibrated in TBS. The proteins were transferred to the membrane using a Bio-Rad semi-dry transfer apparatus at 25 V for 30 minutes. The membrane was then blocked in 1% casein/0.01% sodium azide overnight at 4° or at room temperature for 1 hr, and washed 3 times with TBS. The membrane was incubated with the primary antibody (Cytimmune rabbit IgG a-adenovirus type 5, Lee Biotechnology Research: San Diego, Calif.) at 5 µg/mL (in TBS) for 1 hr at room temperature. Following primary incubation, the membrane was washed 3 times with TBS and incubated with the seco(Amersham Life (Amersham Life Sciences, Arlington Heights, Ill.) Horseradish peroxidase conjugated anti-rabbit Ig) diluted to 1 µL stock antibody/I mL TBS for 1 hr at room temperature. A final three time wash was performed with TBS and the membrane incubated with Amersham ECL detection reagents for 1 minute, exposed in the dark to Hyperfilm-ECL (Amersham) for various times (several seconds to minutes to give a selection of various contrasts) and developed in an X-ray film developer.

Figure 7:
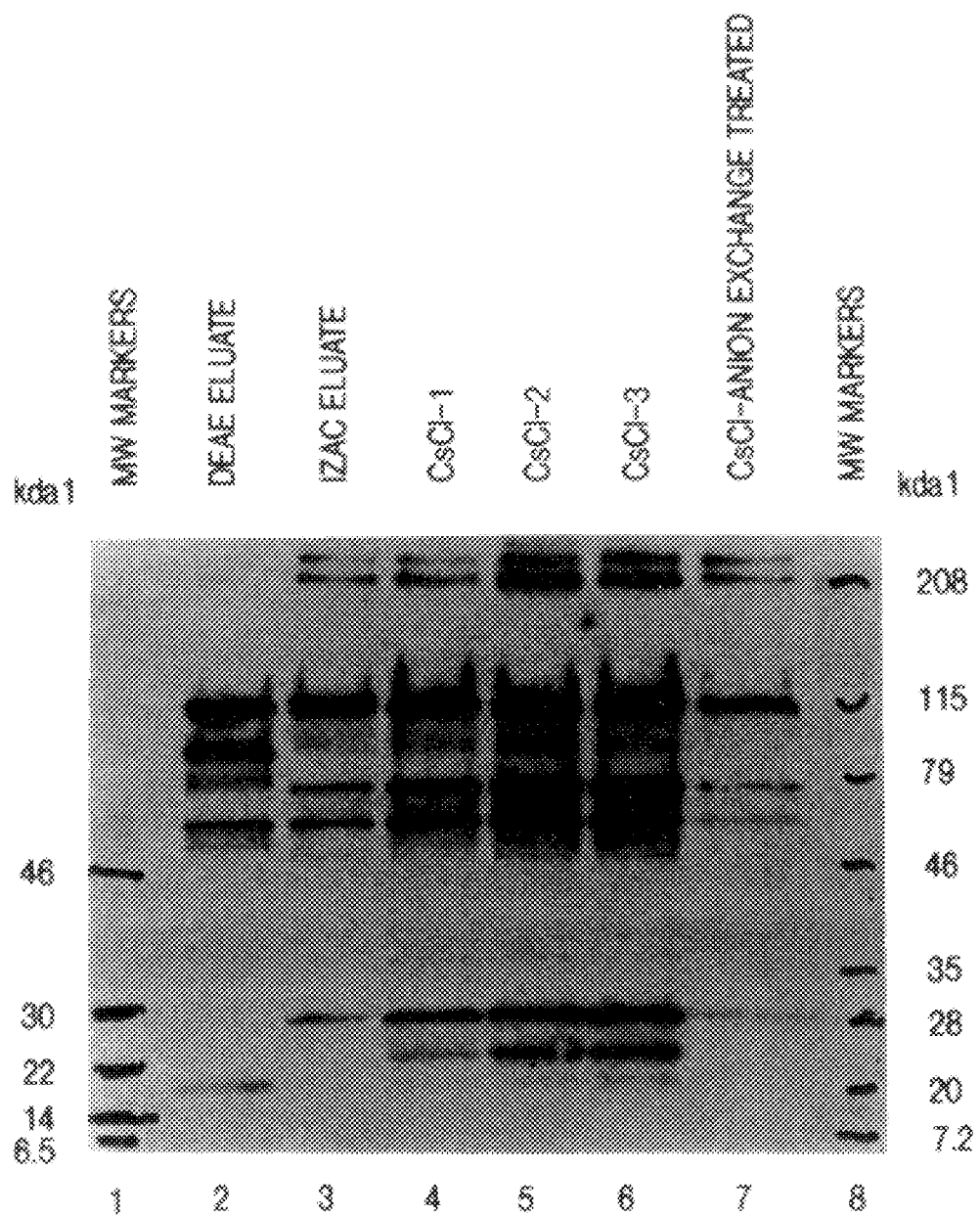
FIG. 7: Western Blot Comparison of ACN53 Derived from Column Chromatography and CsCI-Ultracentrifugation. Samples, identical to those previously described, were electrophoresed on an 8–16% gradient gel and transferred to a PVDF membrane. The blot was incubated first with 5 µg/ml Cytimmune rabbit IgG anti adenovirus type 5 antibody, then with Amersham's horseradish peroxidase conjugated anti-rabbit Ig (NA934) and developed using electrochemical detection.

Using this western blot analysis, differences between banding patterns of ACN53 in various states of purification can be seen in FIG. 7.

Procedure 4

Assay for Recombinant Adenoviral Particle Number by Absorbance at 260nm in Presence of SDS For this measurement, concentrated virus was diluted 1 in 10 in 0.1 % SDS in phosphate buffered saline (PBS). The sample was vortexed for 1 minute and then centrifuged at 14,000 rpm in an Ependorf microfuge to remove any precipitate. A matched pair of cuvettes were blanked with 0.1% SDS in PBS buffer by running a baseline scan on Shimadzu UV160U spectrophotometer (Shimadzu Scientific Instrument, Columbia, MD.). The SDS-treated virus sample was then placed in the sample cuvette and scanned from 220 to 340 nm. If there was absorbance between 310 and 320 nm, the sample was too concentrated and was diluted further and remeasured. The $A_{260}/A_{280}$ ratio was also determined from this scan, and must be between 1.2–1.3 in order to ensure that the product is pure enough to calculate particle number. If this condition is met, the absorbance value at 260 nm only is used to calculate the number of virions/mL. A conversion factor of $1.1 \times 10^{12}$ particles per absorbance unit at 260 nm (Maizel et al., *Virology* 36:115–125 (1968)) was used to calculate particle number with approximately 10% error. Typical values for samples subjected only to Anion Exchange Chromotography (i.e., Examples 1 and 2 using a DEAE resin) were between 1.14 to 1.19. When such samples were subjected to an IZAC as described in Example 3, the ratios were in the 1.22 to 1.25 range.

EXAMPLE 1

Lysis of Unencapulated Nucleic Acids Nuclease Treatment

Infected cell lysate is comprised of contaminants both host-cell and viral in origin. Some of these contaminants were removed prior to chromatography. Specifically, host cell, non encapsulated or incomplete ACN53 nucleic acids were enzymatically degraded at this stage of the process with a nuclease such as Benzonase™. This may be done early in the process for two reasons. Early Benzonase™ treatment resulted in better yields in anion exchange chromatography. Benzonase™ was removed by subsequent process steps. The presence of Benzonase during the process can be assayed by a commercially available ELISA kit (American International Chemical, Natick, Md.)

Clarification of the treated lysate was accomplished by filtration rather than centrifugation. A slow speed spin was used to remove cellular debris (FIG. 1). Filtration was then used to prepare the product for loading onto the first column. The type of filter used (i.e. composition and pore size) and its effective product recovery was assayed by the quantitative anion exchange assay described in Example 3, Procedure A.

Centrifugation was followed by filtration through a Gelman Sciences Acrodisc™ 0.8/0.2 µm 2-stage syringe filter. Recovery of ACN53 depended on the pore size and type of membrane used for filtration. Filters such as polysulfone, PVDF membranes and cellulose acetate based membranes were used. Polysulfone and PVDF were preferred.

The supernatent from this step was made 2 mM in $MgCl_2$, 2% (wt/vol) in sucrose and 2.5% (wt/vol) β-cyclodextrin. Benzonase™ (American International Chemical, Inc.) was added to a final concentration of 100 units/mL and allowed to incubate for 1 hr at room temperature. The treated material was clarified by centrifugation in a Beckman TJ-6 at 3000 rpm for 10 min and filtration through a Gelman Sciences Acrodisc™ 0.8/0.2 µm filter. The resultant supernatant was taken on to Example 2.

EXAMPLE 2

Anion Exchange Chromatography

Overall, the characteristics of DEAE chromatography were found to be consistent, and loading studies with high titer lysate ($3 \times 10^{12}$ ACN53 particles/mL) showed a linear response between volume injected and ACN53 peak area recovered. Elution of a DEAE column by introduction of a linear salt gradient gave three major peaks. The first of these was a protein peak with a $A_{260}/A_{280}$ ratio of ca. 0.5. Next was the ACN53 peak ($A_{260}/A_{280}$=1.23) followed by a DNA ($A_{260}/A_{280}$=2) peak at the end of the gradient. The same three peaks were obtained whether run in a HEPES, Tris buffer or phosphate buffer system. The pH can be varied, however, if run at pH 7.5 using HEPES pH 7.5/NaCl/sucrose/$MgCl_2$ less contaminating material bound to the columns. DEAE chromatography yielded a high degree of initial purification. The immobilized metal ion purification chromatography step removed these contaminants. Column resins were tested for their separation characteristics in 6.6×50 mm (1.7 mL) borosilicate Omnifit™ columns (Omnifit Ltd., Cambridge, England). The columns were mounted on a PerSeptive Bioystems Biocad™ (Cambridge, Mass.) chromatography workstation. The chromatography was monitored on-line for pH, conductivity, and dual wavelength optical density detection at 280 nm and 260 nm.

Anion exchange resins were equilibrated in 50 mM HEPES, pH 7.5, 300 mM NaCl, 2 mM $MgCl_2$, 2% sucrose at 1 mL/min. A 50 mM Tris buffer pH 8.0 (with 300 mM NaCl, 2 mM $MgCl_2$, 2% sucrose) was also used. After the cell lysate was loaded and washed to baseline as monitored by absorbance, elution was performed with a 20 column volume 300–600 mM linear NaCl gradient and collected in 0.5 mL fractions. In preparation for future use, the column was then cleaned with 2 column volumes of 0.5 M NaOH, a 1.5 M NaCl wash and re-equilibrated.

In order to obtain an approximate control retention time, CsCI-ACN53 was injected onto a DEAE column equilibrated in 50 mM Tris pH 8 at 2 mL/min (350 cm/hr) and eluted with a 10 min (11.7 column volume) 0–1.5 M linear NaCI gradient. A single peak was detected with an $A_{260}/A_{280}$ of 1.23. The protein bands present in this fraction reacted with Ad 5 polyclonal antibody upon slot-blot analysis.

Figure 2:
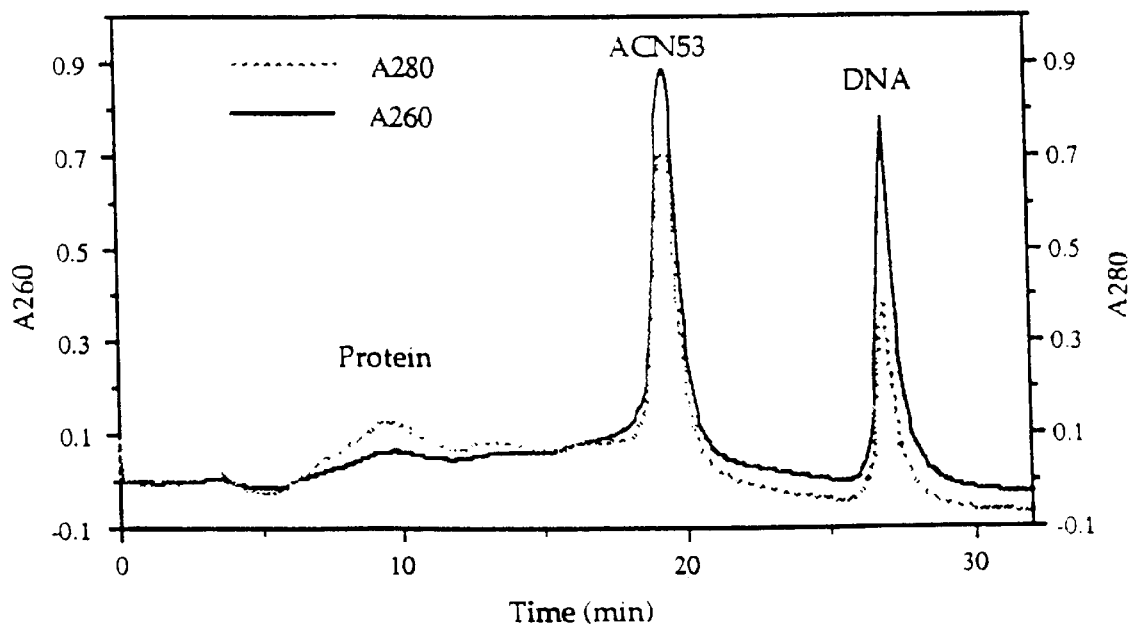
FIG. 2: Identification of ACN53 infected cell lysate components and separated by DEAE chromatography by dual wavelength UV absorbance using their 260/280 nm absorbance ratio.

Several peaks were resolved when an infected cell lysate sample was applied to the DEAE column (FIG. 2). The composition of the peaks were deduced from the $A_{260}/A_{280}$ absorbance ratio. For example, the first peak has an $A_{260}/A_{280}$ ratio of 0.5, and is mainly protein. The third peak has an $A_{260}/A_{280}$ ratio of 2, suggesting that this material was nucleic acid. The ACN53 virus peak eluted second with a ratio of 1.23. The identities of these peaks were confirmed by spiking experiments and by running SDS gels of each peak. In typical experiments using the above conditions an $A_{260}/A_{280}$ ratio of 1.23±0.08 was found to be characteristic of virus peaks.

Figure 3:
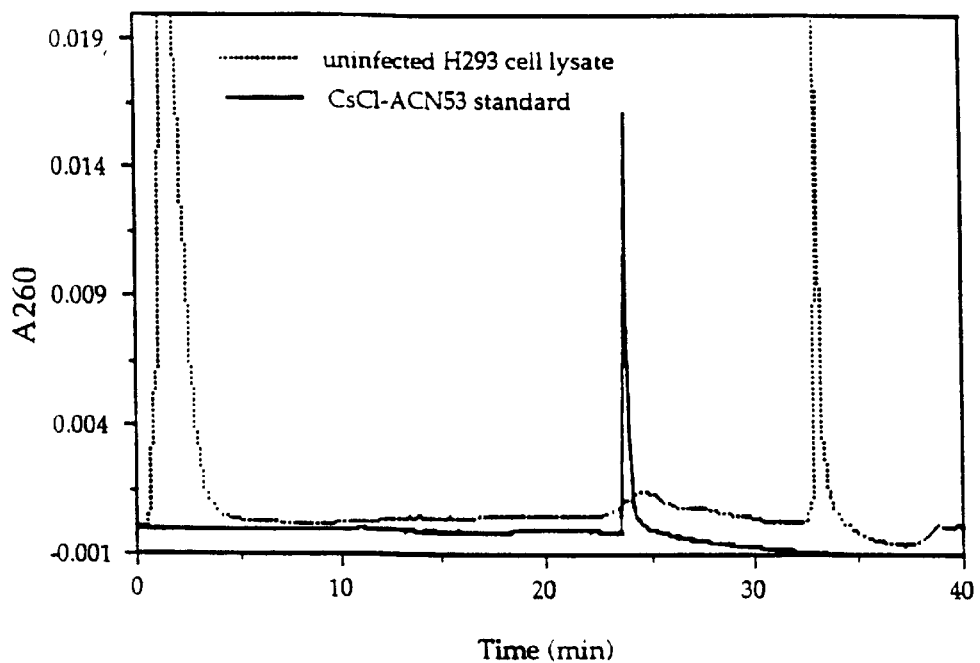
FIG. 3: Comparison of CsCI-ACN53 and host-cell contaminant retention times during DEAE purification. Elution of CsCI-ACN53 is compared to elution of uninfected H293 host-cell lysate blank chromatographed over a DEAE column.

In order to assess the purification capabilities of DEAE chromatography, experiments were performed in which both non-infected ATCC-293 cell lysate and CsCI-ACN53 were applied to the column (FIG. 3). Most of the host cell material either passed through the column during the load or eluted at an earlier retention time than that of ACN53; however, a small peak eluted with the same retention time as ACN53. From these data it appeared that non-viral contamination of the ACN53 peak might be expected from host cell material. Examination of the contaminant peak, the peak eluting last in the cell lysate sample shown in FIG. 3, revealed an $A_{260}/A_{280}$ nm ratio of approximately 2. This indicated that the peak had a high nucleic acid content and could possibly be reduced or eliminated by treatment with nuclease. DEAE runs with and without Benzonase™ pretreatment demonstrated that the enzyme reduced the amount of contamination of host cell material in the ACN53 fraction pool.

EXAMPLE 3

Immobilized Metal Affinity Chromatograph

Immobilized metal affinity chromatography (IMAC) using zinc as the divalent cation (IZAC) gave higher product recovery and did not require any sample manipulation of the DEAE fraction pool prior to loading. Impurities removed by this method eluted in the flow through peak and were well resolved from product, leading to simpler pooling criteria. IZAC was reproducible, and when used with DEAE provided a two column purification protocol capable of delivering pure ACN53 as specified by SDS-PAGE gels and westerns, $A_{260}/A_{280}$ ratios and infectious to non-infectious particle ratios. A summarized overall protocol is as follows:

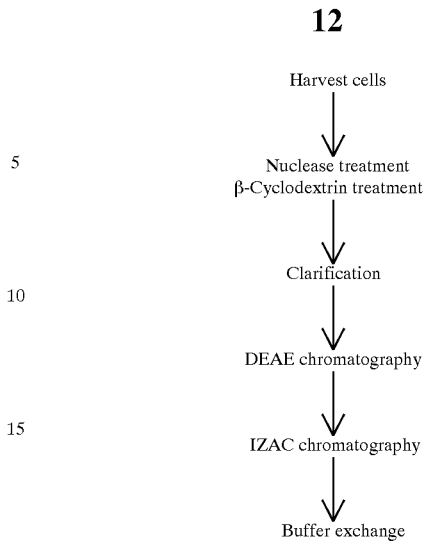

Stepwise recoveries in terms of total particles and infectious units are summarized in Tables 1 and 2 in the experimental section.

The Immobilized zinc affinity chromatography (IZAC) system was prepared for metal charging by washing the column sequentially with 1 volume of 100 mM EDTA and 1 volume of 0.2 M NaOH, flushing with water after each step. The matrix was subsequently charged with zinc by injecting 1 column volume of 100 mM $ZnCl_2$ in $H_2O$ acidified with 0.5 µL/mL glacial acetic acid. The matrix was then thoroughly washed in water prior to equilibration in 50 mM HEPES pH 7.5/450 mM NaCI/2% sucrose/2 mM $MgCl_2$. Sample loading did not require any manipulation; DEAE pool fractions or CsCI derived material could be injected directly onto the column. After loading, the column was washed with a 10 column volume decreasing NaCI linear gradient from 50 mM HEPES pH 7.5/450 mM NaCI/2% sucrose/2 mM $MgCl_2$ to 50 mM HEPES pH 7.5/150 mM NaCI/2% sucrose/2 mM $MgCl_2$. Elution was performed with a linear 0–500 mM glycine gradient (in 150 mM NaCI) applied over 10 column volumes.

Figure 5:
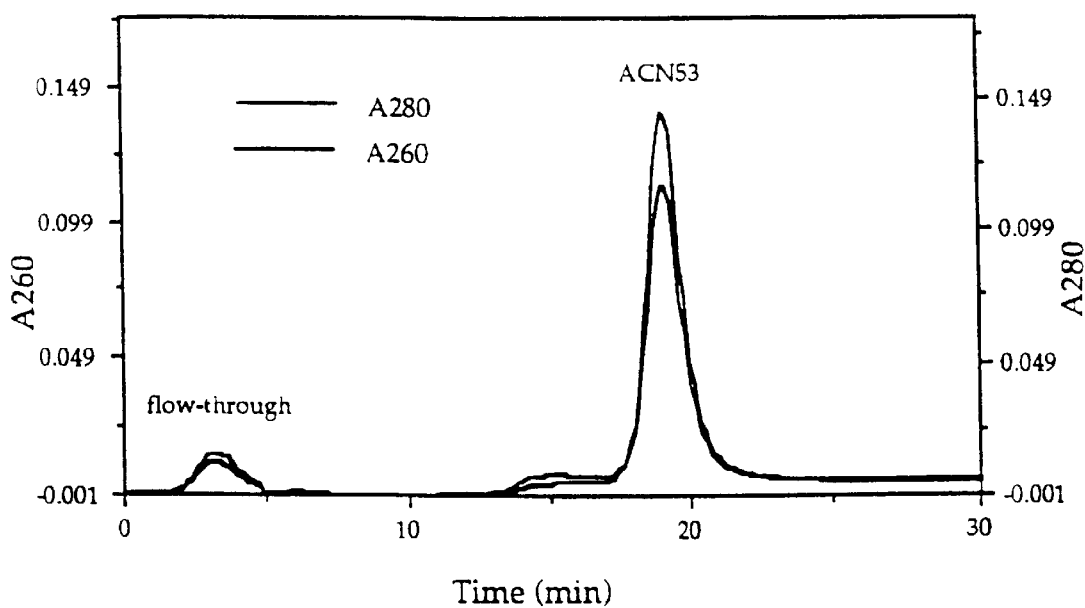
FIG. 5: Immobilized metal affinity chromatography of a DEAE-ACN53 fraction pool. A semi-pure DEAE purified ACN53 fraction pool was injected onto a 6.6×50 mm TosoHaas AF chelate 650M column charged with $ZnCl_2$ and eluted with a linear 0-500 mM glycine gradient.
Figure 4:
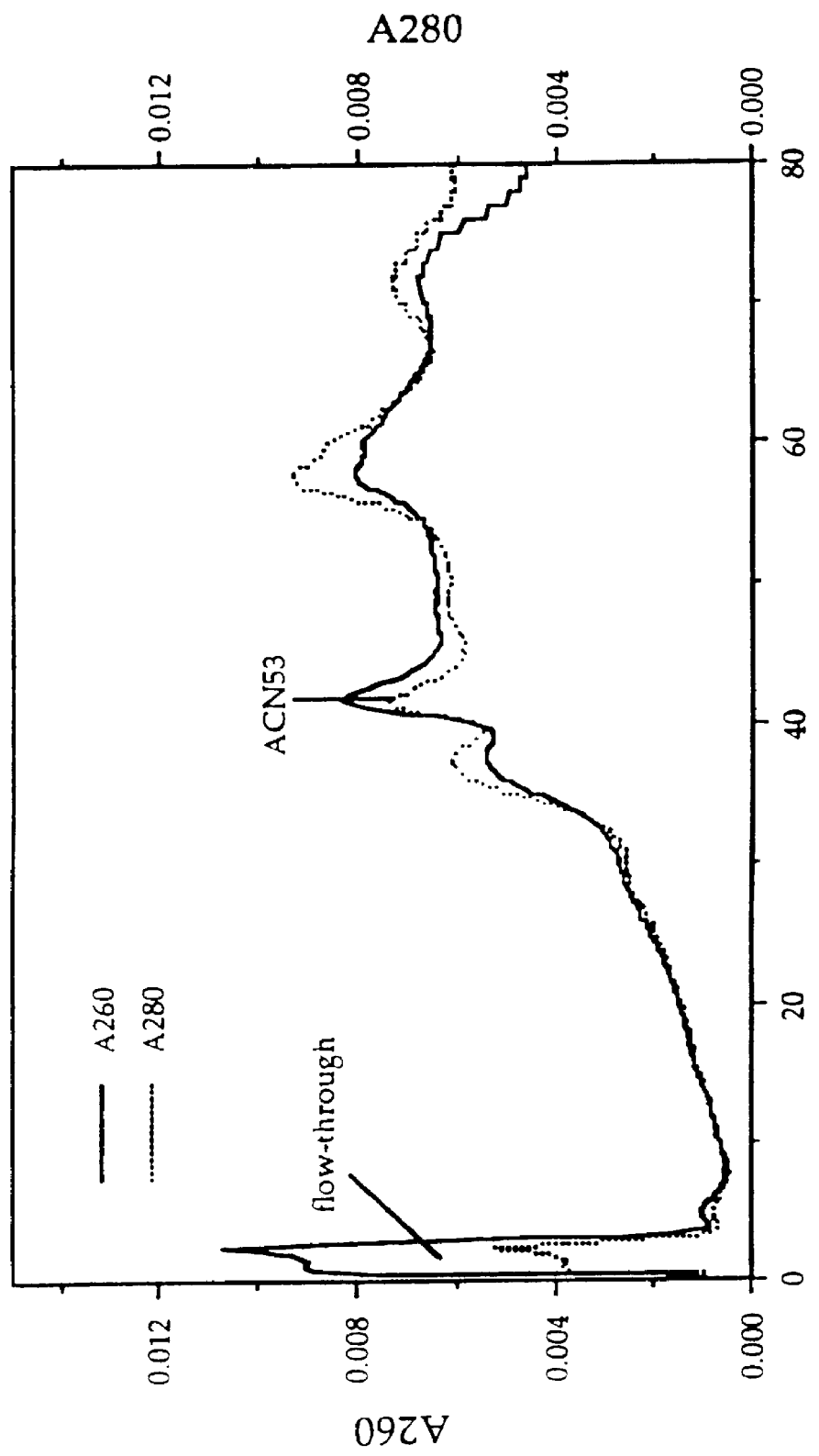
FIG. 4: Butyl-Hydrophobic Interaction Chromatography of a DEAE-ACN53 fraction pool. A semi-pure DEAE purified ACN53 fraction pool was mixed with an equal volume of 50 mM tris/pH 8.0/3 M ammonium sulfate and injected onto a TosoHaas Butyl-650M column and eluted with a 1.5–0 M decreasing ammonium sulfate gradient.

The interaction of ACN53 with a metal affinity column was shown to be metal specific (with zinc preferred); injection of CsCI-ACN53 onto an uncharged column (a column not pre-loaded with zinc) resulted in a shift of the product peak to the flow through. An ACN53-DEAE from Example 2 fraction pool purified over IZAC is shown in FIG. 5. Analysis of an IZAC fraction pool produced a yield of 49–65% and an $A_{260}/A_{280}$ ratios of 1.22–1.25. A gel and western blot comparison of CsCI-ACN53, DEAE purified and DEAE/IZAC purified material can be seen in FIGS. 6 and 7. The CsCI-ACN53 and DEAE/IZAC materials were very similar, and the DEAE-only purified material was less pure by these criteria.

The effect of different IZAC buffer and elution systems was evaluated by splitting a DEAE-ACN53 pool in half and purifying both halves over IZAC in HEPES pH 7.5 and Tris pH 8 buffer systems. IZAC was also run in the presence of sucrose and $MgCl_2$ without affecting the separation. The use of copper as the metal ion and imidazole as the elution agent were also tested (for a general review of metal affinity chromatography, see Belew et.al. 1987; Kato etal. 1986). Various systems: zinc/glycine, zinc/imidazole, copper/glycine and copper/imidazole, all worked on the metal affinity purification columns. ACN53 can be eluted using a pH 7 to pH 9 gradient.

A: Assay for Recombinant Adenoviral Particle Number by Anion Exchange HPLC

A 1 mL Resource Q- (Pharmacia, Piscataway, N.J.) anion exchange column was used to quantitate the number of viral particles in various samples. The column was equilibrated in 300 mM NaCl, 50 mM HEPES, pH 7.5. at a flow rate of 1 mL/min on a Waters 625 chromatography system equipped with 717 plus autosampler and a 991 photodiode array detector (PDA). The chromatography was monitored on the PDA detector (Milford, Mass.) scanning from 210 to 300 nm. A standard curve was constructed by injecting CsCl purified ACN53 virions characterized for total particles at a selected absorbance, $A_{260}$ in 0.1%SDS.

The assay was independent of injected sample volume. After the sample loaded, the column was washed with two column volumes of equilibration buffer followed by a linear gradient from 300 to 600 mM NaCl in 50 mM HEPES, pH 7.5, over 10 column volumes. The gradient was followed with a 2 column volume wash with 600 mM NaCl in 50 mM HEPES, pH 7.5. After each chromatographic run, the column was cleaned with 2.6 column volumes of 1.5 M NaCl in 50 mM HEPES, pH 7.5, and then re-equilibrated for the next injection. The column was cleaned more vigorously after injection of crude samples by injecting 0.25 to 1 column volume of 0.5 N NaOH followed by a wash with 1.5 M salt. Injecting NaOH and then running the gradient was a convenient way to accomplish cleaning. The use of such an assay in measuring the total number of adenovirus particles present are set forth in the following Table 1.

TABLE 1

Yield and Purity Data Based on Total ACN53 Particles

| Step | Viral Particle #/mL[a] | Vol. (ml) | Total Particles | Step Yield[b] | Total Yield[b] |
|---|---|---|---|---|---|
| Lysate (Procedure 2) | $6 \times 10^{11}$ | 5.0 | $3 \times 10^{12}$ | 100% | |
| DEAE load (Example 1) | $6 \times 10^{11}$ | 5.0 | $3 \times 10^{12}$ | | |
| DEAE eluate (Example 2) | $4 \times 10^{11}$ | 5.0 | $2 \times 10^{12}$ | 67% | |
| IZAC load (Example 3) | $4 \times 10^{11}$ | 3.8 | $1.52 \times 10^{12}$ | | |
| IZAC eluate[c] (Example 3) | $2.38 \times 10^{11}$ | 3.0 | $7.14 \times 10^{11}$ | 47% | 31% |

[a]As determined by Analyzical Ion Exchange
[b]In terms of viral particle number
[c]After dialysis into final formulation B: Buffer Conditions A variety of buffer conditions have been used in the purification of ACN53 by column chromatography in this study in the pH range of 7.0–8.0. (e.g. Seth *Virology* 68:1204–1206 (1994)). Checking for degradation at various pH limits is accomplished by assaying for degradation by TCID50 (Procedure C below) and analytical anion exchange analysis (Procedure A above). The effect of buffer salt concentration on the viability of ACN53 showed that abrupt changes of ionic strength can lead to loss of virus. Salt concentration should be carefully controlled and monitored.

C: Measurement of Infectious Recombinant Adenovirus Particles by $TCID_{50}$ Assay The quantitation of infectious Adenovirus Type 5 particles, before, during and after the purification methods taught in these Examples is accomplished by an end point titer assay (tissue culture infective dose-50%; abbreviated $TCID_{50}$). (See Philipson, *Virology* 15:263–268 (1961)). Reagents, a materials list and instructions are available from Chemicon International, Inc. (cat.# 3130: "Adenovirus Direct Immunofluorescence Assay", Temecula, Calif.).

ATCC 293 cells were plated into a 96-well plate: 100 μL of $5 \times 10^5$ cells/mL for each well in complete MEM (10% bovine calf serum; 1% glutamine) media. In a separate plate, a 250 μL aliquot of virus sample diluted $1:10^6$ was added to the first column and is serially diluted two-fold across the plate. One row was reserved for a positive control (CsCl-purified ACN53); one for a negative control. A 100 μL aliqout of each well was transferred to its identical position in the ATCC-293 seeded plate and allowed to incubate a 37° in a humidified incubator for 2 days. The media was then decanted by inversion and the cells were fixed with the addition of 50% acetone/50% methanol. After washing with PBS, the fixed cells were incubated for 45 min with a FITC labeled anti-ad5 antibody (Chemicon International #5016) prepared according to the kit instructions. After washing with PBS, the plate was examined under a fluorescent microscope (490 nm excitation, 520 nm emission) and scored for the presence of label. The titer was quantitated using the Titerprint Analysis program (Lynn, *BioTechniques*, 12:880–881 (1994)). Results from assays performed in accordance with this procedure are set forth in the following Table 2, which Table includes a ratio calculated using the values from Table 1 above.

TABLE 2

Yield and Purity Data Based on Infective ACN53 Particles

| Step | Step Yield ($TCID_{50}$) | $A_{260}:A_{280}$ Ratio | Viral Particle Purity by HPLC at $A_{280}$ |
|---|---|---|---|
| Lysate | — | — | 3% |
| DEAE load | 49% | 1.17 | 92% |
| IZAC Eluate | 44% | 1.23 | 98% |

The ratio of total virus particles to infectious viral particles can vary widely from preparation to preparation. Values for CsCl derived viruses in the range of 60 to 80. The calculation of this ratio in crude lysates or semi-pure fractions has been made possible by the anion exchange particle assay (see Example 3[A]). Using analytical anion exchange changes in the ratio of ideal virus particles to infectious virus particles can be monitored. Using the purification method of this invention the total virus particle to infectious virus particle ratio of the crude lysate and subsequently purified material is comparable to that obtained using ultracentrafugation. Within the error of the assay these values are equivalent. By this criteria, chromatographic purification is well tolerated by the virus. By other criteria, namely SDS-PAGE and western blot analysis (FIGS. 6 and 7), chromatographic purification is superior to ultracentrifugation based methods.

Figure 8:
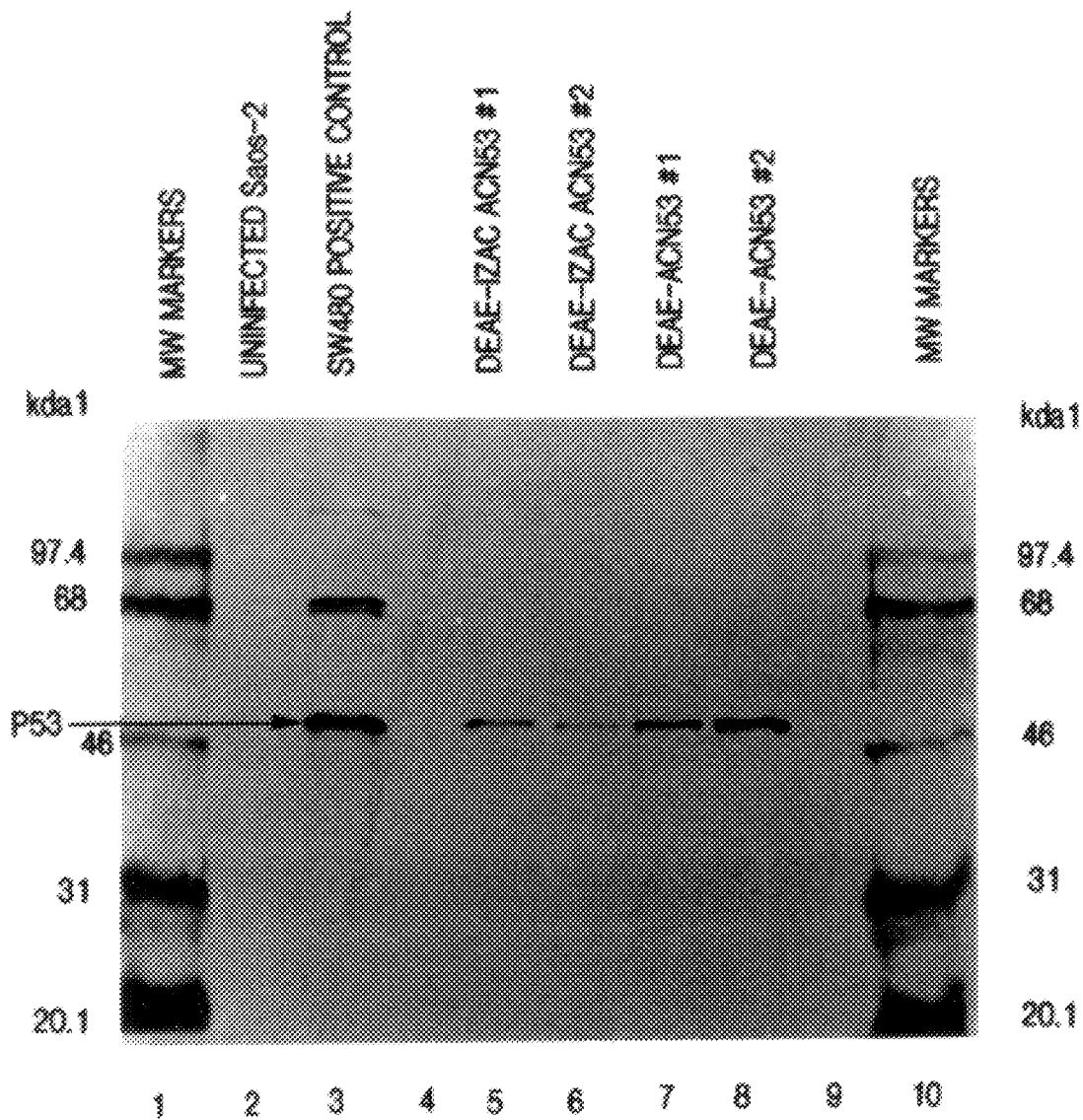
FIG. 8: Expression of p53 gene product in Saos-2 cells. Two different lots of chromatographically produced ACN53 were assayed by western blot for their ability to effect gene transfer to p53-null Saos-2 cells. The semi-pure DEAE fractions are shown in lanes 7 & 8, the final product in 5 & 6. P53-expressing SW480 cells were used as a positive control; uninfected Saos-2 cells were used as a negative control.

D: Assay for Infectious Recombinant Adenovirus Particles by Expression of P53 Protein The activity of virus preparations was also tested by assaying for the expression of the p53 gene product in Saos-2 cells, a p53-negative osteosarcoma cell line. Saos-2 cells were seeded into a 6-well tissue culture plate at a concentration of $5 \times 10^5$ cells/well in 3 mL of media: Kaighn's nutrient mixture F12: DME High Glucose (1:1 mixture), supplemented with 2 mM L-glutamine and 10% fetal bovine serum. The cells were incubated in humidified air, 7±1% $CO_2$ at 37° for 16–24 hrs. The spent media were removed and replaced with 1 mL of fresh media, and the cells were infected at 20,40, or 60 MOI of purified virus. After incubation for 1 hr, an additional 2 mL of media is added and allowed to incubate for 8 hrs. The cells were then washed once with Dulbecco's-PBS and lysed by adding of 250 μL of: 50 mM tris/0.5% Noridet P-40/250 mM NaCl/5 mM EDTA/5 mM NaF/5 μg/mL Leupeptin and 5 μg/mL Aprotinin/2 mM PMSF. The plate was incubated on ice for 5 min after which the lysates were transferred to individual 1.7 mL microcentrifuge tubes. They were spun down for 45 sec at 14000 rpm in a microfuge and the supernatants were assayed for the presence of p53 protein by western blot analysis with the primary anti-p53 monoclonal antibody 1801 (Vector Laboratories, Burlingame, Calif.) and a 1:1 mixture of sheep anti-mouse IgG-HRP and streptavidin-HRP (Amersham). The p53 protein band was detected using Amersham's ECL detection kit according to the manufacturer's instructions. The results of the use of such assay are shown in FIG. 8. p53 expression can be seen in ACN53 purified only by DEAE chromatography as well as by both DEAE and IZAC chromatography. (The lower levels of expression in lanes 5 and 6 are due to the fact that these samples were run at a lower MOI than the DEAE samples.)

E: Host Cell Protein Contamination

Host cell contamination was assessed by western blot analysis using polyclonal antibodies developed against ATCC-293 cell components. Polyclonal antibodies were commercially obtained and were raised against various 293 cellular antigens (HTI, Ramona, Calif.). The results indicated that the final products of either CsCl or DEAE-IZAC purification contained no detectable host cell contaminants. In the case of semi-pure DEAE-ACN53, there was a small amount of immunogenic contamination seen in the product pool: 3 major bands and several minor ones. The majority of host cell contamination is recovered in the flow-through portion of the DEAE step. Contaminants which copurified with ACN53 in the DEAE step were removed by zinc affinity chromatography, and were recovered in IZAC flow-through fractions prior to the introduction of the glycine gradient.

F: SDS-PAGE Analysis Samples Containing Recombinant Adenovirus Particles

For Coomassie blue staining, 100–200 μL of an adenovirus containing sample (at approximately $1 \times 10^{11}$ particles/mL) was collected, desalted by trichloroacetic acid precipitation or by dialysis followed by concentration in a speed-vac. The sample was then resuspended in SDS-PAGE reducing buffer (125 mM Tris-HCL, pH 6.8, 20% glycerol, 4% (w/v) SDS, 0.005% bromophenol blue, 0.5% β-mercaptoethanol) to approximately 30 μL, boiled for 5 min and loaded onto a 1 mm×10 well Novex 8–16% gradient Tris-Glycine minigel. Samples were electrophoresed for 1.5 hrs at 140 V. The gel is then fixed in 40% methanol/10% acetic acid for 30 min, and then Coomassie stained with the Pro-Blue staining system (Integrated Separation Systems, Natick Mass.) according to the vendor's procedure.

Gels to be silver stained were loaded with 5–15 μL of sample. The sample was boiled with an equal volume of reducing buffer and electrophoresed as described for Coomassie detection. Fixing was performed by treating the gel in 10% trichloroacetic acid for 1 hr followed by a 3× wash in water purified to 18 megohms. The gel was stained with the Daiichi silver staining kit according to the instructions provided (Integrated Separation Systems).

EXAMPLE IV

Vector Infectivity, Transfer of Therapeutic Gene

Figure 6:
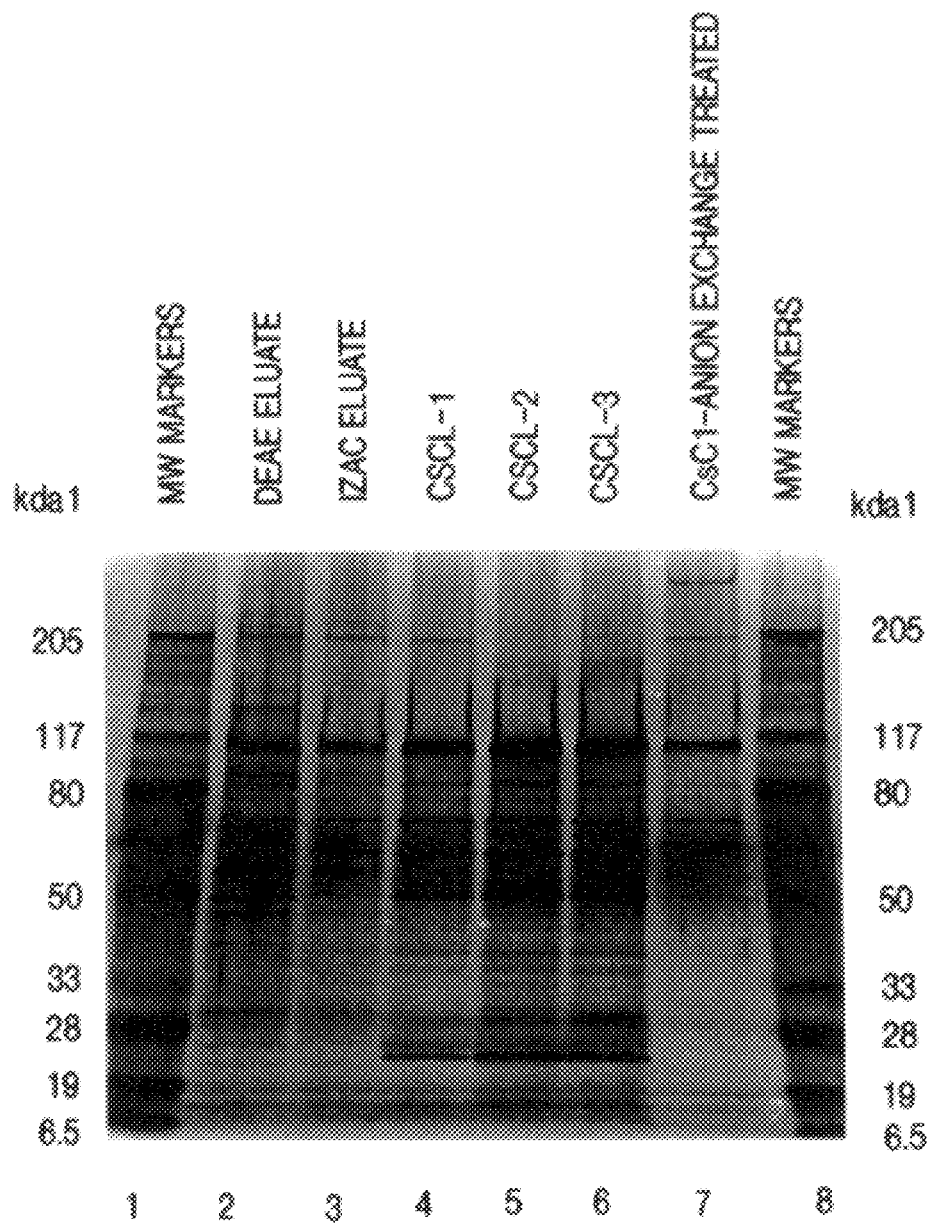
FIG. 6: SDS-PAGE comparison of ACN53 derived from column chromatography and CsCI-ultracentrifugation. Samples were electrophoresed on an 8–16% gradient polyacrylamide gel and silver stained for analysis. Lanes 2 and 3 are DEAE and IZAC eluate pools respectively. Lanes 4–6 represent 3 different lots (CsCI-1, CsCI-2, and CsCI-3) of CsCI-ACN53 run side by side in order to examine lot to lot consistency. Lane 7, CsCI-ion exchange treated lot, represents the ACN53 peak recovered when a sample of CsCI-ACN53 derived ion-exchange treated lot is purified over a Resource Q anion exchange HPLC column (Resource Q, Pharmacia). Lanes 1 and 8 are standard molecular weight markers.

Characterization of DEAE-IZAC-ACN53 has shown that virions retained their infectivity during chromatographic treatment as measured by TCID50 analysis (Table 1,2) and were able to effect gene transferred as assayed by P53 protein expression in Saos-2 cells (FIG. 8). Comparison of this DEAE-IZAC-ACN53 to CsCl-ACN53 in SDS-PAGE analysis has shown that there were more lower molecular weight protein bands present in the CsCl-ACN53 (FIGS. 6 and 7). Side-by-side comparison of different CsCl-ACN53 lots has shown some batch-to-batch variability whereas chromatographically produced material has been very consistent. The total to infectious particle ratio and absorbance spectrum of both types of material are directly comparable. Characterization of chromatographically produced ACN53 in terms of purity and activity have shown that a 1 day 2-column procedure can replace a 3 day ultracentrifugation protocol.

A preferred purification scheme for ACN53 as shown above is to treat 1s infected cell lysate with Benzonase™ prior to the chromatographic steps. Clarification is then accomplished by step filtration through 0.8 μm followed by 0.2 μm membranes. If necessary, a larger pore (e.g. 5 μm) prefiltration step can be added for more viscous suspensions. Adjustment to pH 7.5/300 mM NaCl is then performed in preparation for loading onto a DEAE column. The product peak, as detected by the $A_{260}/A_{280}$ nm ratio or the characteristic photo-diode array spectrum, is pooled and directly injected onto a zinc-charged, iso-osmotically equilibrated metal affinity column. The ionic strength of the buffer is then gradually lowered to approximate phosphate-buffered saline (ca,150 mM NaCl) prior to elution of product with a glycine gradient. This material is then dialyzed into the final formulation.

We claim:

1. A method for purification of an intact viral particle from a cell lysate, the method comprising:
    a) treating said cell lysate which contains said intact viral particle with an enzymatic agent that selectively degrades both unencapsulated DNA and RNA;
    b) chromatographing the treated lysate from step a) on a first resin; and
    c) chromatographing the eluant from step b) on a second resin;
wherein one resin is an anion exchange resin and the other is an immobilized metal ion affinity resin.

2. The method of claim 1, wherein the first resin is an anion exchange resin and the second resin is an immobilized metal affinity resin.

3. The method of claim 1, which comprises the additional step of filtering the treated lysate from step (a).

4. The method of claim 1, which comprises the additional step of buffering the pH of the cell lysate between about 5.0 and about 9.0 before applying it to the first resin.

5. The method of claim 1, wherein the viral particle is a retrovirus.

6. The method of claim 1, wherein the viral particle is an adenovirus.

7. The method of claim 6, wherein the adenoviral particle is a recombinant viral particle which comprises a tumor suppressor gene.

8. The method of claim 1, wherein the adenoviral particle is a type 2 or type 5 adenovirus.

9. The method of claim 8, wherein the adenoviral particle is a type 5 adenovirus.

10. The method of claim 7, wherein the tumor suppressor gene is a wild-type p53 gene.

11. The method of claim 1, wherein the anion exchange resin is chosen from the group consisting of DEAE, TMAE, DMAE, QAE and PEI.

12. The method of claim 11, wherein the anion exchange resin is DEAE resin.

13. The method of claim 1, wherein the immobilized metal affinity resin is charged with a divalent cation of a metal chosen from the group consisting of cobalt, nickel, copper, and zinc.

14. The method of claim 13, wherein the immobilized metal affinity resin is a TED or an IDA resin.

15. The method of claim 14, wherein the immobilized metal affinity resin is an IDA-(cross-linked agarose) resin.

16. The method of claim 13, wherein the divalent cation is zinc.

17. The method of claim 1, wherein the enzymatic agent that selectively degrades both unencapsulated DNA and RNA is one or more enzymes.

18. The method of claim 17, wherein the one or more enzymes are endonucleases.

19. The method of claim 18, wherein the enzyme is a mixture of RNase and DNase.

20. A method for purification of intact viral particles from a cell lysate, the method comprising the steps of:

a) treating said cell lysate which contains said intact viral particle with an enzymatic agent that selectively degrades both unencapsulated DNA and RNA;

b) chromatographing the treated lysate from step a) on a first resin, and c) chromatographing the eluant from step b) on a second resin;

wherein:

one resin is an anion exchange resin and the other is a hydrophobic interaction chromatography resin; or one resin is a cation exchange resin and the other is either a hydrophobic interaction chromatography resin or an immobilized metal ion affinity resin.

21. The method of claim 20, wherein one resin is an anion exchange resin and the other is a hydrophobic interaction chromatography resin.

22. The method of claim 21, wherein the first resin is an anion exchange resin and the second is a hydrophobic interaction chromatography resin.

23. The method of claim 20, wherein one resin is a cation exchange resin and the other is an immobilized metal ion affinity resin.

24. The method of claim 20, wherein one resin is a cation exchange resin and the other is a hydrophobic interaction chromatography resin.

25. A method of determining the number of intact viral particles in a sample, the method comprising:

a) chromatographing the sample containing the intact viral particles on an anion exchange resin;

b) monitoring the absorbance of the eluate from the chromatography of step (a) at a selected wavelength; and c) determining the total number of intact viral particles in the sample by comparing the absorbance value obtained in step (b) to a standard curve which relates absorbance to number of viral particles.

26. The method of claim 25, wherein the anion exchange resin has QAE groups covalently attached to a polystyrene/divinyl benzene copolymer support.

27. The method of claim 25, wherein the method further comprises chromatographing the eluate from the chromatography of step (a) on a second resin, wherein the second resin is an immobilized metal ion affinity resin.

* * * * *